(12) United States Patent
Kortan et al.

(10) Patent No.: US 9,296,665 B2
(45) Date of Patent: Mar. 29, 2016

(54) SYNTHESIS OF DROP-IN LIQUID FUELS AND CHEMICALS FROM METHANOL, ETHANOL OR SYNGAS USING MIXED CATALYSTS

(71) Applicant: Pioneer Energy, Lakewood, CO (US)

(72) Inventors: Adam M Kortan, Golden, CO (US); Michael T Kelly, Lakewood, CO (US); Heather A Rose, Lakewood, CO (US); Robert M Zubrin, Golden, CO (US)

(73) Assignee: Pioneer Energy Inc., Lakewood, CO (US)

( * ) Notice: Subject to any disclaimer, the term of this patent is extended or adjusted under 35 U.S.C. 154(b) by 0 days.

(21) Appl. No.: 14/103,615

(22) Filed: Dec. 11, 2013

(65) Prior Publication Data

US 2014/0171691 A1 Jun. 19, 2014

Related U.S. Application Data

(60) Provisional application No. 61/737,019, filed on Dec. 13, 2012, provisional application No. 61/750,263, filed on Jan. 8, 2013, provisional application No. 61/778,861, filed on Mar. 13, 2013.

(51) Int. Cl.
| | |
|---|---|
| *C07C 41/09* | (2006.01) |
| *C07C 1/22* | (2006.01) |
| *C07C 41/00* | (2006.01) |
| *C10G 50/00* | (2006.01) |
| *C10G 3/00* | (2006.01) |

(52) U.S. Cl.
CPC . *C07C 1/22* (2013.01); *C07C 41/00* (2013.01); *C10G 3/45* (2013.01); *C10G 3/49* (2013.01); *C10G 50/00* (2013.01); *C10G 2400/02* (2013.01); *Y02P 30/20* (2015.11)

(58) Field of Classification Search
USPC ........................................................ 568/698
See application file for complete search history.

(56) References Cited

U.S. PATENT DOCUMENTS

| | | | |
|---|---|---|---|
| 4,547,601 A * | 10/1985 | Holland et al. | 585/310 |
| 6,489,528 B2 | 12/2002 | Drake et al. | |
| 2002/0099249 A1 | 7/2002 | Drake et al. | |
| 2010/0144907 A1* | 6/2010 | Kibby et al. | 518/714 |
| 2010/0185033 A1 | 7/2010 | Karim et al. | |
| 2010/0229725 A1* | 9/2010 | Farsad et al. | 96/74 |
| 2011/0036756 A1* | 2/2011 | White | B01J 29/166 208/136 |
| 2011/0152594 A1 | 6/2011 | Brown | |

FOREIGN PATENT DOCUMENTS

| | | | |
|---|---|---|---|
| WO | WO 2012/174205 | * | 12/2012 |
| WO | WO 2012174205 A1 | | 12/2012 |

OTHER PUBLICATIONS

James J. Spivey (1991): Review: Dehydration Catalysts for the Methanol/Dimethyl Ether Reaction, Chemical Engineering Communications, 110:1, 123-142.
Synergism in Acetic Acid/Methanol Reactions Over YZSM-5 Zeolites; Clarence D. Chang Prepr. Pap.—Am. Chem. Soc., Div. Fuel Chem.; (United States); Journal vol. 28:2; Conference: 185. American Chemical Society national meeting, Seattle, WA, USA, Mar. 20, 1983.
Final Report (MTG) http://chemelab.ucsd.edu/methanol/memos/final.html.

* cited by examiner

*Primary Examiner* — Scarlett Goon
*Assistant Examiner* — Ana Z Muresan
(74) *Attorney, Agent, or Firm* — John T. Henri; Daniar Hussain (57) ABSTRACT

The present invention discloses a system for converting methanol or synthesis gas to liquid hydrocarbons with comparable energy content to gasoline within a mixed bed single reactor or double reactor systems. Varying catalyst composition and temperature profiles allow for significant tailoring of reaction conditions to the specific feedstocks or the desired products.

16 Claims, 6 Drawing Sheets

Figure 1. Single reactor methanol conversion system with an optional recycle loop.

Figure 2. Single reactor methanol conversion system with an optional hydrogen separation membrane.

Figure 3. Dual reactor methanol conversion system with an optional recycle loop and hydrogen separation membrane.

Figure 4. Single reactor syngas conversion system.

Figure 5. Dual reactor syngas conversion system.

Figure 6. Single reactor alcohol conversion system.

SYNTHESIS OF DROP-IN LIQUID FUELS AND CHEMICALS FROM METHANOL, ETHANOL OR SYNGAS USING MIXED CATALYSTS

REFERENCE TO RELATED APPLICATIONS

This application is a non-provisional of and claims the benefit of U.S. Provisional Application Ser. No. 61/737,019, filed on 13 Dec. 2012 entitled "Synthesis of Fuels from Methanol or Syngas Using Mixed Catalysts," U.S. Provisional Application Ser. No. 61/750,263, filed on 8 Jan. 2013 entitled "Synthesis of Fuels from Ethanol or Mixtures of Ethanol with Methanol or Water Using Mixed Catalysts," and U.S. Provisional Application Ser. No. 61/778,861, filed 13 Mar. 2013 entitled "Synthesis of Isopropanol and Olefins" all of which are incorporated in their entireties herein by reference.

BACKGROUND OF THE INVENTION

The statements in this section merely provide background necessary to understand the invention and may not be prior art.

Petroleum has been the primary source of transportation fuels for the last century and continues to heavily dominate the market today. Many economic, political and environmental factors contribute to the desire for alternatives to petroleum for the essential transportation fuels. Various alternative fuels are being examined, but almost all require substantial modifications or additions to the current infrastructure.

Examples of fuels considered include alcohols such as methanol and ethanol, but they require both vehicle modifications and a new distribution infrastructure as they are corrosive to existing infrastructure. Examples of other fuels considered include CNG (compressed natural gas) and LNG (liquified natural gas), but these require even more extensive engine modifications, bulky and expensive fuel tanks, and complete changes to the refueling infrastructure. Other fuels considered include higher alcohols such as butanol but they have a lower energy density than gasoline.

For 40 years, a process of converting methanol to gasoline (MTG) has been known. This process would allow for production of a gasoline fuel that requires no major infrastructure modifications while allowing for a larger and more flexible resource base. Since methanol can be produced from a huge variety of sources including natural gas, coal, and biomass, it is an attractive process but has yet to see significant applications due to the relatively low cost of petroleum products.

Unfortunately, the MTG process requires multiple steps, including first transforming methanol to dimethyl ether, then transforming dimethyl ether to propylene, and finally transforming propylene to gasoline. This multi-stage system adds complexity and cost to the MTG process. As a result, the MTG process is not economically attractive, except when oil prices are extremely high. Thus, there is a need to develop an economic means for conversion of methanol to gasoline.

Ethanol is a major product used as a fuel and chemical produced both from renewable and petroleum and natural gas feed stocks. The ethanol to gasoline (ETG) process requires multiple steps, first transforming ethanol to diethyl ether, then transforming diethyl ether to ethylene, and finally transforming ethylene to gasoline. This multistage system adds complexity and cost to the ETG process. Additionally, ethanol from fermentation sources is difficult to fully purify as the dehydration process cannot be completed with simple distillation. As a result the ETG process is not economically attractive, except when oil prices are extremely high. Thus there is a need to develop an economic means for conversion of ethanol to gasoline.

Due to the parity in the MTG and ETG processes, it is possible to combine the two alcohols in any ratio and still achieve highly efficient conversion to gasoline. The ability to freely mix alcohols allows for a wide range of potential alcohol sources. Water can also be mixed with the ethanol feed, and while it may be thermodynamically unfavorable it is still possible to achieve efficient conversion. The tolerance of water in the feed could allow for drastically reduced ethanol costs since the ethanol could be utilized before undergoing several costly distillation and drying steps.

The present invention allows for high-efficiency conversion of ethanol, mixtures of ethanol and methanol, or mixtures of methanol and ethanol and water to aromatic compounds usable as gasoline in one step, in one pass, within a single mixed catalyst reactor. Such a system allows for radically lower plant costs since fewer independent reactors, condensers, valves, pipes, pumps, transducers, and control system elements are used, and combining catalysts leads to higher one-pass conversions and a reduction in the total material required. The fuels produced from this system are high energy products that are readily compatible with the existing transportation fuel infrastructure.

Therefore, it would be an advancement in the state of the art to provide a system and method for converting methanol and/or ethanol and/or mixtures thereof to gasoline-type aromatic hydrocarbons (hereinafter referred to as "gasoline").

It is against this background that various embodiments of the present invention were developed.

BRIEF DESCRIPTION OF THE INVENTION

The present invention discloses novel methods to synthesize hydrocarbons.

In one embodiment, an alcohol is reacted over a mixed catalyst bed in a single reactor charged with a dehydration catalyst and a zeolite catalyst. In another embodiment, a method to synthesize dimethyl ether catalytically from a $H_2/CO$ syngas mixture using a single reactor containing a homogenous mixture of a methanol production catalyst and a methanol to dimethyl ether synthesis catalyst is described. The methanol production catalyst may be a single metal or metal oxide, or a combination such as Cu—ZnO. The methanol to dimethyl ether catalyst may be methanol dehydration catalyst such as gamma-alumina.

In another embodiment, a method to synthesize gasoline boiling range hydrocarbons is described where, $H_2/CO$ syngas mixture is reacted using a single reactor containing a homogenous mixture of a methanol production catalyst, a methanol to dimethyl ether synthesis catalyst and a dimethyl ether to hydrocarbon catalyst.

In another embodiment, a method to synthesize gasoline boiling range hydrocarbons catalytically from a $H_2/CO$ syngas mixture using two reactors is described. The reaction of synthesis gas $H_2/CO$ in the first reactor containing a homogenous mixture of a methanol production catalyst and a methanol to dimethyl ether synthesis catalyst to form dimethyl ether and reaction of dimethyl ether in the second reactor containing dimethyl ether to hydrocarbon catalyst to form the gasoline boiling range hydrocarbon product is described.

In another embodiment, a method to synthesize gasoline boiling range hydrocarbons from a light olefin using a single reactor charged with a zeolite catalyst is described.

DETAILED DESCRIPTION OF THE INVENTION

In one embodiment, the present invention allows for high-efficiency conversion of methanol to aromatic compounds usable as gasoline in one step, in one pass, within a single mixed catalyst reactor. Such a system allows for radically lower plant costs since fewer independent reactors, condensers, valves, pipes, pumps, trandsducers, and control system elements are used, and combining catalysts leads to higher one-pass conversions and a reduction in the total material required. Additionally, modifying the mixed catalyst ratios allows for much easier tunability of the process conditions, either in response to the feedstock composition or for the desired products. The fuels produced from this system are high energy products that are readily compatible with the existing transportation fuel infrastructure.

The present invention involves a system for passing a feed of methanol into a single fixed bed reactor containing a mixed catalyst capable of converting the methanol into aromatic hydrocarbons in the gasoline boiling range. The system converts methanol efficiently into desired products by combining a catalyst to dehydrate methanol to dimethyl ether and a catalyst to convert the dimethyl ether as it is produced into aromatic hydrocarbons. By intimately mixing the catalyst in a single reactor the products from dehydration can immediately undergo further reactions and drive the thermodynamic equilibrium forward.

In one embodiment of the present invention, because of the advantages of the described process, the invention is compact enough to be packaged into a semi-trailer and transported to locations where waste streams are readily available. For example, the present invention may be packaged into a portable trailer that may be taken to a site of a flare gas well (such as the hundreds of flare gas wells in the Bakken formation in North Dakota) and utilized to convert the wasted flare gas into valuable gasoline.

In another embodiment, there is provided a method for the manufacture of fuels and chemicals by providing an ethanol feed into a single fixed bed reactor containing a mixed catalyst capable of converting the gas into aromatic hydrocarbons in the gasoline boiling range. The system is able to produce high ethanol conversion efficiency into the desired products by combining a catalyst to dehydrate an alcohol to its corresponding ether and a catalyst to convert the ether as it is produced into aromatic hydrocarbons. By intimately mixing the catalyst in a single reactor the products from dehydration can immediately undergo further reactions and drive the thermodynamic equilibrium forward.

In another embodiment of this system a mixture of methanol and ethanol can be used as the feedstock. The same catalysts for the single component systems can be used and any ratio of methanol and ethanol can be used.

In another embodiment of this system a mixture of ethanol and water can be used as the feedstock. The system is tolerant to a large range of ethanol/water mixtures, and the system can be adjusted to produce consistent ethanol space velocities with high conversion regardless of the concentration of the feed.

In one embodiment, a gamma-alumina catalyst is used in this work for the dehydration of methanol and ethanol to their ether derivatives, but other catalysts that perform the same function could be used.

In one embodiment, a transition metal doped ZSM-5 catalyst is used for the conversion of dehydration products of methanol and ethanol to aromatics respectively.

In one embodiment, a transition metal mixed with a main group metal and doped on ZSM-5 to form a catalyst used for the conversion of dehydration products of methanol and ethanol to aromatics respectively.

In one embodiment, a transition metal selected from the group consisting of copper, zinc, iron, manganese, cobalt, zirconium is doped on ZSM-5 to form a catalyst used for the conversion of dehydration products of methanol and ethanol to aromatics respectively.

In one embodiment, a mixture of two or more transition metals are doped on ZSM-5 to form a catalyst used for the conversion of dehydration products of methanol and ethanol to aromatics respectively.

A preferred catalyst used is a transition metal such as zinc, but other metals may also be used.

The catalysts in this system can either be homogenously mixed in a variety of ratios, or can be mixed as a gradient. Increased percentages of dehydration catalyst such as gamma-alumina at the inlet that gradually decrease down the length of the reactor can provide increased alcohol dehydration initially but taper into a majority of metal doped zeolite once the methanol has been converted.

In one embodiment, to make catalyst preparation and loading easier, multiple zones of variably mixed catalyst can be employed in the reactor to make any gradient desired.

Figure 1:
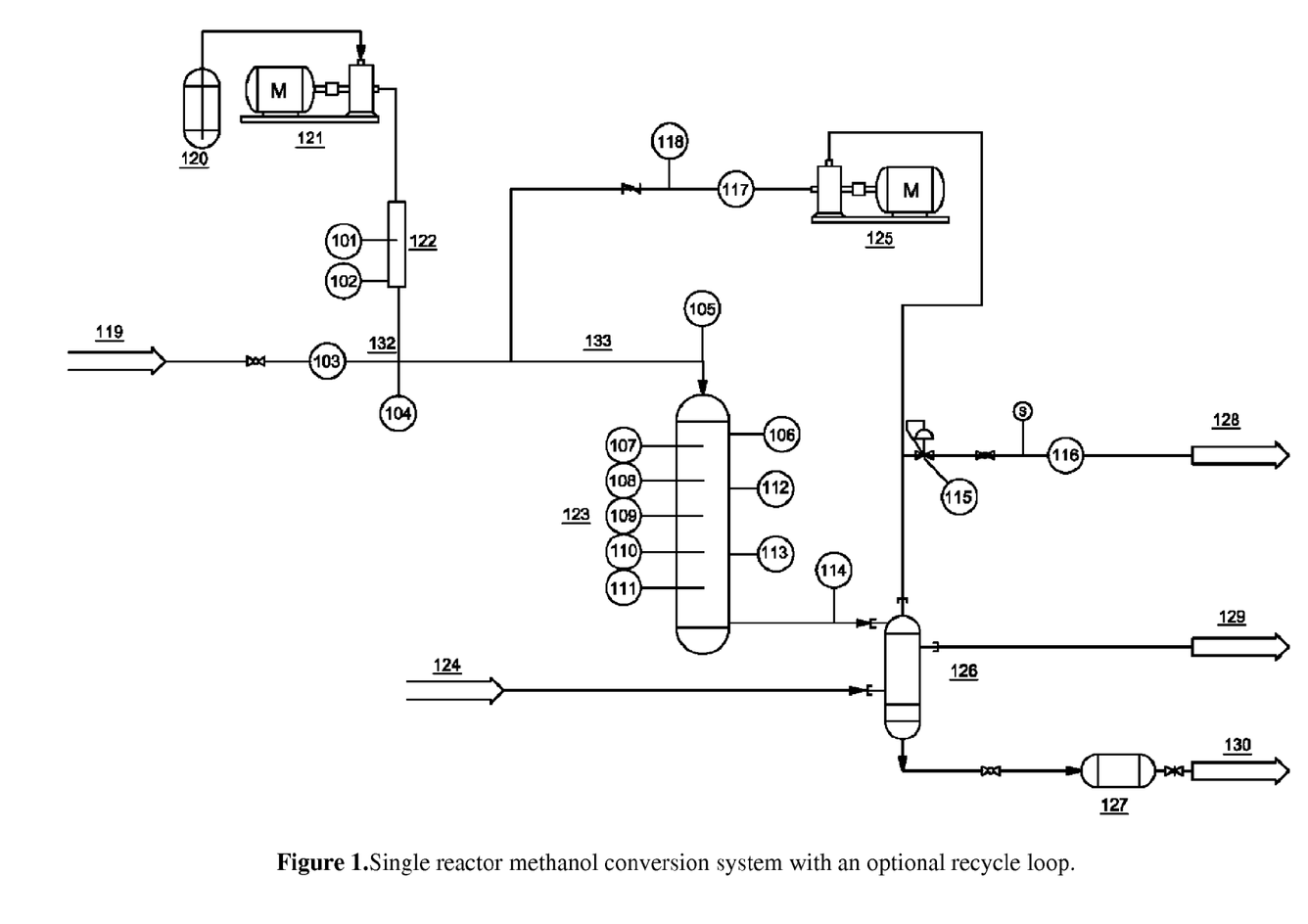
FIG. 1 describes the single reactor methanol conversion system with an optional recycle loop.

In another embodiment of this reaction a recirculating pump is used to recycle the waste gas back into the reactor inlet, as shown in FIG. 1. This allows for the upgrading of small hydrocarbon products that would otherwise be completely lost as waste products. It also allows for controlling the space velocity of the gas through the system, which can be used to modify the kinetics or be useful in controlling the temperature of the reactor.

Figure 2:
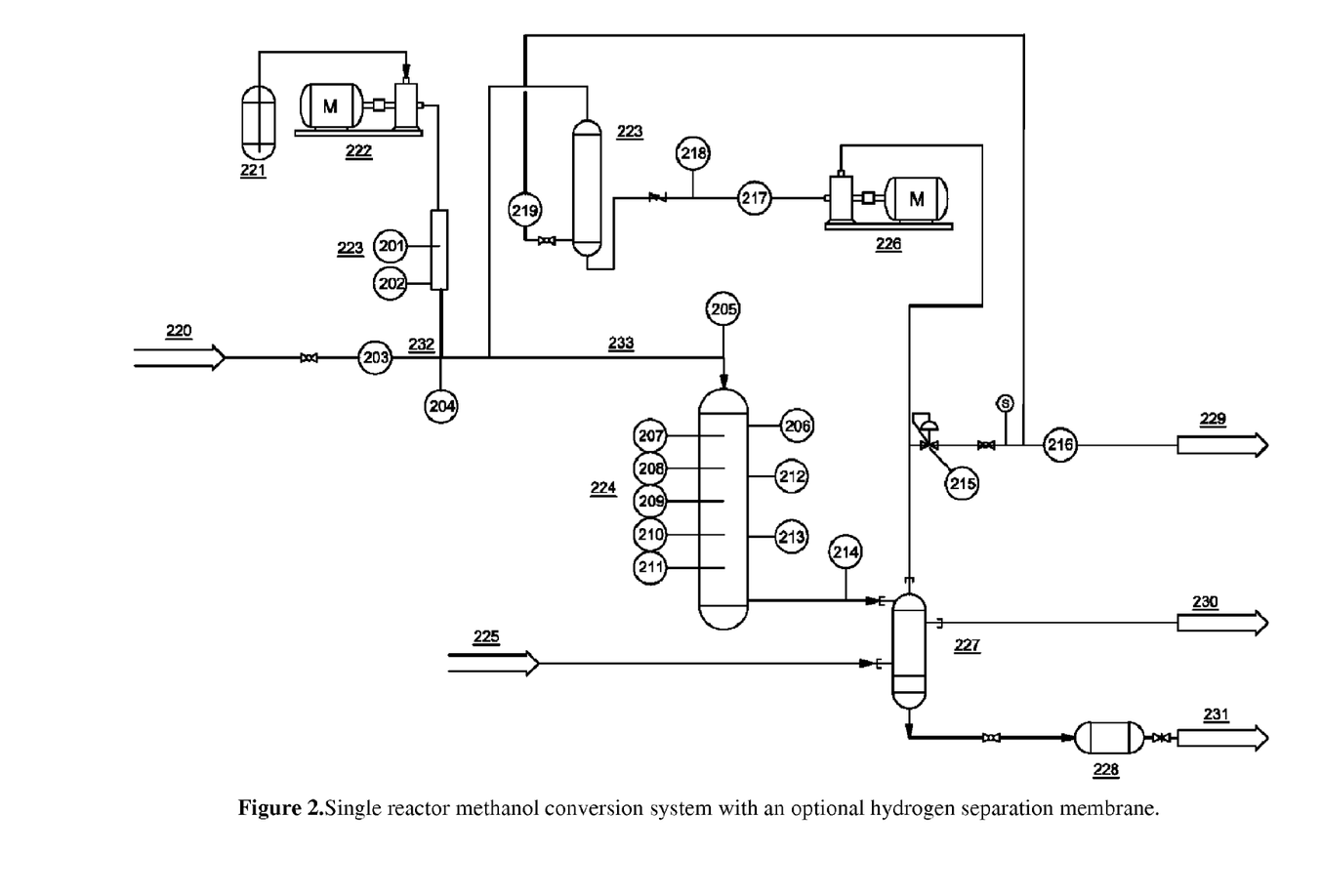
FIG. 2 describes the single reactor methanol conversion system with an optional hydrogen separation membrane.

In another embodiment, a hydrogen separation membrane can also be used in conjunction with the recirculating pump as shown in FIG. 2. By removing the product hydrogen the partial pressure of the hydrocarbons in the recycle stream is increased and the aromatization reaction, which produces hydrogen as a product, would be more thermodynamically driven towards the products.

In another embodiment of this reaction, additional reactors can be utilized after the initial mixed bed reactor in order to further increase the conversion of small gaseous hydrocarbons. Since the feed methanol is essentially completely converted into dimethyl ether or larger products in the first reactor, the secondary reactors would likely contain only a metal doped zeolite catalyst. A condenser that removes water and liquid hydrocarbons from the product stream of the primary reactor would allow for increased conversion in the secondary reactors since the main products of the conversion have been removed from the process stream.

As an addition to this embodiment a recirculating pump can be used to recycle the waste gas stream into the secondary reactors, further increasing the yield of the desired liquid products. Also, a hydrogen separation membrane can be installed in-between the primary and secondary reactors to increase the potential product yields from the secondary reactors, and be used by itself or in conjunction with the recycle loop.

This invention can also be used with feedstocks besides methanol and ethanol including C1 to C5 alcohols as they are available.

In one embodiment, carbon monoxide and hydrogen or synthesis gas (syngas) conversion is preferred. Carbon monoxide conversion to larger hydrocarbons requires a metal catalyst such as copper, chromium, iron, nickel, rhodium, ruthenium, zinc, or their oxides among others to convert the syngas to methanol, and then subsequent reactions further transform the intermediate methanol to aromatic hydrocarbon products.

In one embodiment, a common methanol production catalyst such as Cu—ZnO can be intimately combined with both a methanol dehydration catalyst such as gamma-alumina and a hydrocarbon synthesis catalyst such as metal doped ZSM-5. This process, shown in FIG. 4, allows for an improved CO conversion to methanol thermodynamic equilibrium and greater efficiencies. The intimately mixed catalyst can accomplish the full conversion from syngas to aromatics in a single reactor.

In another embodiment, the ratios of the three component catalyst mixture can be modified within the reactor to achieve greater conversion. By increasing the proportion of methanol production catalyst at the inlet the whole system can make better use the available reactants, and as the CO is converted less of the catalyst is needed down the length of the reactor. This alteration of the catalyst ratios within the reactor could be continuous or could be separated into two or more distinct zones for easier mixing and loading of the reactor.

In another embodiment of this system a secondary reactor containing a catalyst such as metal doped ZSM-5 could be employed after the primary reactor to further convert small organics to more desirable larger products.

In one embodiment of the present invention, because of the advantages of the described process, the invention is compact enough to be packaged into a semi-trailer and transported to locations where waste streams are readily available. For example, the present invention may be packaged into a portable trailer that may be taken to a site of a flare gas well (such as the hundreds of flare gas wells in the Bakken formation in North Dakota) and utilized to convert the wasted flare gas into valuable chemical and fuel products.

In another embodiment of the system, a methanol synthesis catalyst and a methanol dehydration catalyst can be mixed in a single reactor to produce dimethyl ether as an end product. The feed ratio and catalyst composition can be altered to produce dimethyl ether and water using a 2/1 hydrogen/carbon monoxide syngas ratio or the ratio can be altered to 1/1 to facilitate the water gas shift reaction and produce dimethyl ether and carbon dioxide as primary products. The products can be condensed out of the gas stream and separated if necessary using standard distillation techniques.

In another embodiment of the system a syngas stream with additional components such as carbon dioxide or nitrogen can be used.

In another embodiment of the system, two reactors may be employed, with the first reactor containing a mixture of the methanol production catalyst and the methanol dehydration catalyst and the second reactor containing a hydrocarbon synthesis catalyst such as the metal doped ZSM-5. In such a system, the first reactor converts the syngas at high efficiency into dimethyl ether and water or dimethyl ether and carbon dioxide. After the water is knocked out in a condenser, the remaining dimethyl ether can then be converted to aromatics in the metal-doped ZSM-5 reactor.

In another embodiment of the system a light olefin gas such as ethylene or propylene from a variety of sources can be converted to aromatics and larger hydrocarbons by passing them through a transition metal doped zeolite catalyst. The resulting liquid products can be used directly as a fuel.

In another embodiment of the system the light olefin feed can be a mixture of ethylene and propylene in any ratio.

In another embodiment of the invention, propylene is synthesized by the steps of ketonizing acetic acid to form acetone, hydrogenating acetone to form isopropanol and dehydrating isopropanol to form propylene.

In one embodiment of the present invention, because of the advantages of the described process, the invention is compact enough to be packaged into a semi-trailer and transported to locations where waste streams are readily available. For example, the present invention may be packaged into a portable trailer that may be taken to a site of a flare gas well (such as the hundreds of flare gas wells in the Bakken formation in North Dakota) and utilized to convert the wasted flare gas into valuable gasoline.

DEFINITIONS

Unless specifically noted otherwise herein, the definitions of the terms used are standard definitions used in the art. Exemplary embodiments, aspects and variations are illustrated in the figures and drawings, and it is intended that the embodiments, aspects and variations, and the figures and drawings disclosed herein are to be considered illustrative and not limiting.

As used herein, an "alkyl" group is a straight, branched, cyclic, acylic, saturated or unsaturated, aliphatic group or alcoholic group having a chain of carbon atoms. A $C_1$-$C_{20}$ alkyl or $C_1$-$C_{20}$ alkanol, for example, may include alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. An alkyl group may also be represented, for example, as a —$(CR^1R^2)_m$— group where $R^1$ and $R^2$ are independently hydrogen or are independently absent, and for example, m is 1 to 8, and such representation is also intended to cover both saturated and unsaturated alkyl groups.

An "alkyl compound(s)" as used herein, is an alkyl containing 1 to 20 carbons ($C_1$-$C_{20}$ alkyl), and includes cyclic and acyclic alkanes, alkenes, alcohols, ketones and aromatics (e.g., benzene, toluene, ethyl benzene etc.) and mixtures thereof. The alkyl compound may be used as a raw material for chemical processing, a solvent or the alkyl compound may be used as a fuel or mixtures of fuels. Such fuel or mixtures of fuels may be further combined with other fuel or fuel products to form a gasoline. Non-exclusive examples of an alkyl compound include butane, 1-butanol, 2-butanol, 2-pentanol, 1-hexanol, 2-hexanol, 2-heptanol, 4-heptanol, 4-heptanone, 3-methyl cyclohexanol, 2,6-dimethyl-4-heptanol and mixtures thereof.

"Gasoline" is known to comprise of a complex mixture of volatile hydrocarbons suitable for use as a fuel in a spark-ignition internal combustion engine. Typically, gasoline boils over a range of about 27° C. to about 225° C. Gasoline may consist of a single blendstock, such as the product from a refinery alkylation unit, or it may comprise of a blend of several blendstocks. The blending of gasoline is well known in the art and may include a combination of three to twelve or more different blendstocks. Optimization of the blending process takes into account a plurality of characteristics of both the blendstocks and the resulting gasoline, and may include such characteristics as cost and various measurements of volatility, octane, boiling point characteristics and chemical composition. While hydrocarbons usually represent a major component of gasoline, certain oxygen containing organic compounds may be included as gasoline components. In one aspect, such oxygen containing organic compounds are referred to as "oxygenate" or "oxygenates," and are important gasoline substitutes such as ethanol and butanol. Oxygenates are also useful as components in gasoline because they are usually of high octane and can be a more economical source of gasoline octane than a high octane hydrocarbon blending component such as alkylate or reformate.

Natural gas liquids are the larger hydrocarbon components of natural gas, including ethane, propane and butane as the major constituents. These components can be separated from the methane using simple condensation. This liquid portion of the natural gas stream can be used as is or further separated using common chemical engineering techniques.

Catalysts used in reductions may be supported or unsupported. A supported catalyst is one in which the active metal or metals are deposited on a support material; e.g. prepared by soaking or wetting the support material with a metal solution, spraying or physical mixing followed by drying, calcination and finally reduction with hydrogen if necessary to produce the active catalyst. Catalyst support materials used frequently are porous solids with high surface areas such as silica, alumina, titania, magnesia, carbon, zirconia, zeolites etc.

The dehydration of alcohols can be accomplished using several catalysts including metal oxides and concentrated acids. Gamma alumina is an efficient solid catalyst used for this process. Dehydration of methanol generally forms dimethyl ether while larger alcohols such as ethanol and propanol form their corresponding ethers as well as olefins such as ethylene and propylene.

Zeolites are crystalline aluminosilicates with ordered, porous structures with well defined pore sizes. Zeolites generally consist of a tetrahedral network of $SiO_2$ and $Al_2O_3$ linked through the oxygen sites. The silica to alumina ratio can be varied, which changes the acidic character of the zeolite. The excess negative charge generated by the aluminum ions is balanced by a counter cation, which is usually sodium or ammonia in the most simple form. Alternatively, the zeolite can be doped with a metal cation which displaces the counter cation and alters the properties of the catalyst. This doping is usually done using the incipient wetness impregnation technique, which consists of adding a metal salt dissolved in the minimum amount of water to the zeolite, heating to allow diffusion, then drying and calcining to achieve the final catalyst. ZSM-5 has a pore size of 5.4-5.6 angstroms. Zeolite catalysts have been used for many applications, including extensive study into using them as sole catalysts of the methanol to gasoline process.

The methods of the present invention can comprise, consist of, or consist essentially of the essential elements and limitations of the method described herein, as well as any additional or optional ingredients, components, or limitations described herein or otherwise useful in synthetic organic chemistry.

"Synthesis gas" or "syngas" is a mixture of varying amounts of carbon monoxide and hydrogen. Syngas maybe produced by the partial oxidation of materials such as methane, liquid hydrocarbons, coal, biomass, etc.

"Biomass" is material obtained from living or recently living organisms.

Acetic acid may be made by oxidation of ethanol produced by fermentation or conversion of synthesis gas to methanol followed by its carbonylation. Synthesis gas may be obtained in large quantities from biomass, coal, natural gas, etc.

DETAILED DESCRIPTION OF DRAWINGS

FIG. 1 describes a single reactor methanol conversion system where methanol from a liquid reservoir (120) is delivered via an HPLC pump (121) into a vaporizer (122) heated with heat tape. Gas flow is mixed with an inert gas from a cylinder (119) and controlled by a mass flow controller (103). Mixed gas flow can be preheated with heat tape (131-132). Heated gas enters the reactor (123) heated with heat tape then passes to the condenser (126) cooled with a coolant loop (124, 129). Liquid from the condenser is captured in a sample cylinder (127) and proceeds to liquid product analysis (130). Gas from condenser passes through a back pressure regulator (115), is measured by a dry gas meter (116) and is vented out and analyzed (128). Optionally, the gas can also be recirculated via a recirculating compressor (125) with flow measured by a mass flow meter (117) and returned to the reactor inlet. Pressure is monitored by pressure transducers (106, 118) and temperature is monitored by thermocouples (101-102, 104-105, 107-114).

FIG. 2 describes a single reactor methanol conversion system where methanol from a liquid reservoir (221) is delivered via an HPLC pump (222) into a vaporizer (223) heated with heat tape. Gas flow is mixed with an inert gas from a cylinder (220) and controlled by a mass flow controller (203). Mixed gas flow can be preheated with heat tape (232-233). Heated gas enters the reactor (224) heated with heat tape then passes to the condenser (227) cooled with a coolant loop (225, 230). Liquid from the condenser is captured in a sample cylinder (228) and proceeds to liquid product analysis (231). Gas from condenser passes through a back pressure regulator (215), is measured by a dry gas meter (216) and is vented out and analyzed (229). Optionally, the gas can also be recirculated via a recirculating compressor (226) with flow measured by a mass flow meter (217) and passed through a membrane gas separator (223). Permeate gas flow is measured by a mass flow meter (219) then vented out of the system. Retenate gas is returned to the reactor inlet. Pressure is monitored by pressure transducers (206, 218) and temperature is monitored by thermocouples (201-202, 204-205, 207-214).

Figure 3:
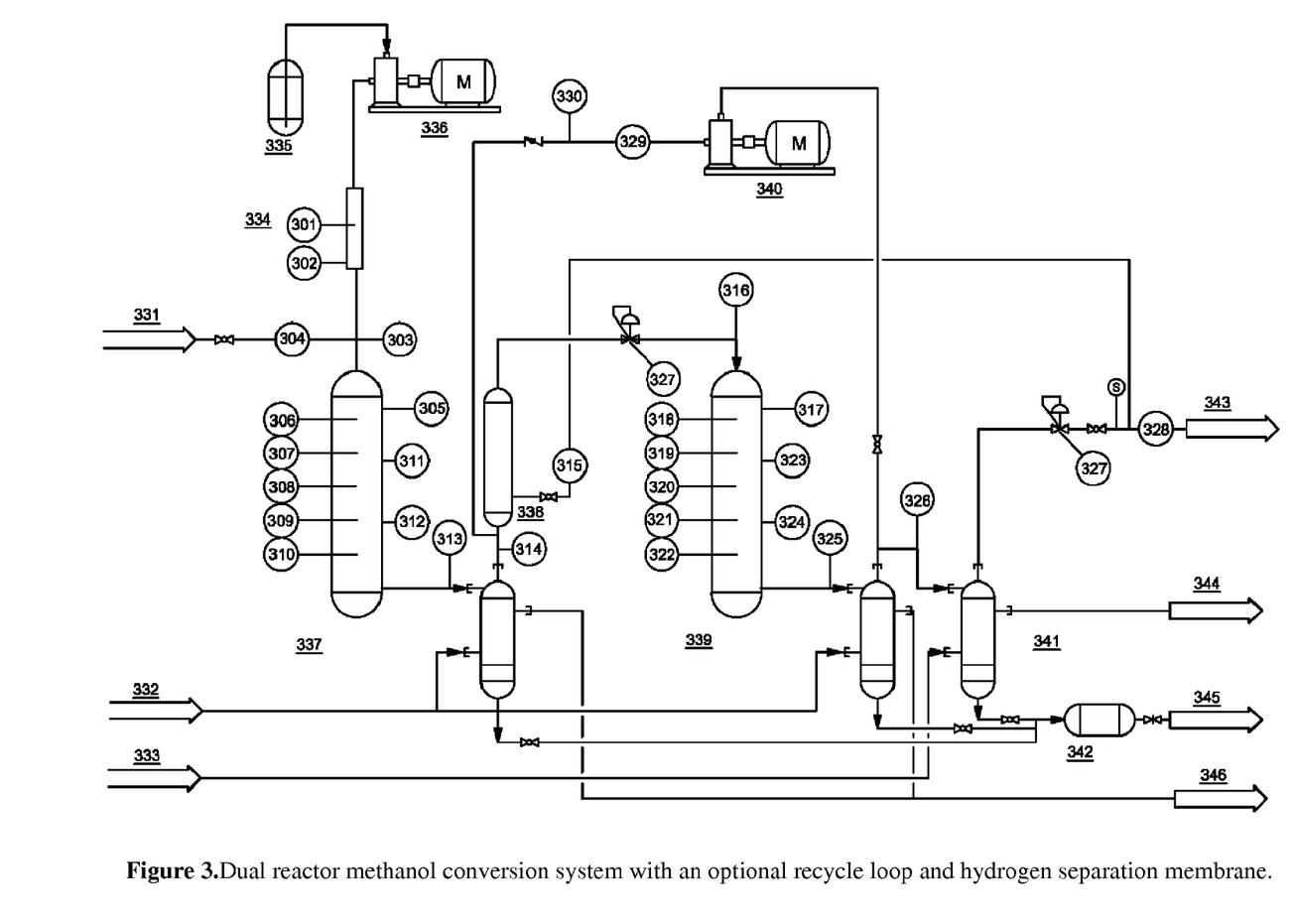
FIG. 3 describes the dual reactor methanol conversion system with an optional recycle loop and hydrogen separation membrane.

FIG. 3 describes a dual reactor methanol conversion system where methanol from a liquid reservoir (335) is delivered via an HPLC pump (336) into a vaporizer (334) heated with heat tape. Gas flow is mixed with an inert gas from a cylinder (331) and controlled by a mass flow controller (304). Mixed gas enters the first reactor (337) heated with heat tape then passes to the first condenser cooled with cold house water loop (332, 346). Gas from condenser passes through a gas separation membrane (338) where the permeate is monitored by a mass flow meter (315) and vented while the retenate passes through a back pressure regulator (327) and enters the second reactor (339) which is heated by heat tape. After the second reactor the gas stream passes through the second cold water cooled condenser and the remaining gas passes through a third condenser (341) which is chilled by a coolant loop (333, 344). Liquid from all three condensers is collected in a sample cylinder (342) and removed from the system for liquid analysis (345). The gas from the cold condenser passes through a back pressure regulator (327), measured by a dry gas meter (328) and is vented from the system and analyzed (343). Optionally, some of the gas can be recirculated using a recirculating pump (340) and measured by a mass flow meter (329) and returned to the process stream at the inlet to the gas separation membrane. Pressure is monitored by pressure transducers (305, 317, 330) and temperature is monitored by thermocouples (301-303, 306-314, 316, 318-326).

Figure 4:
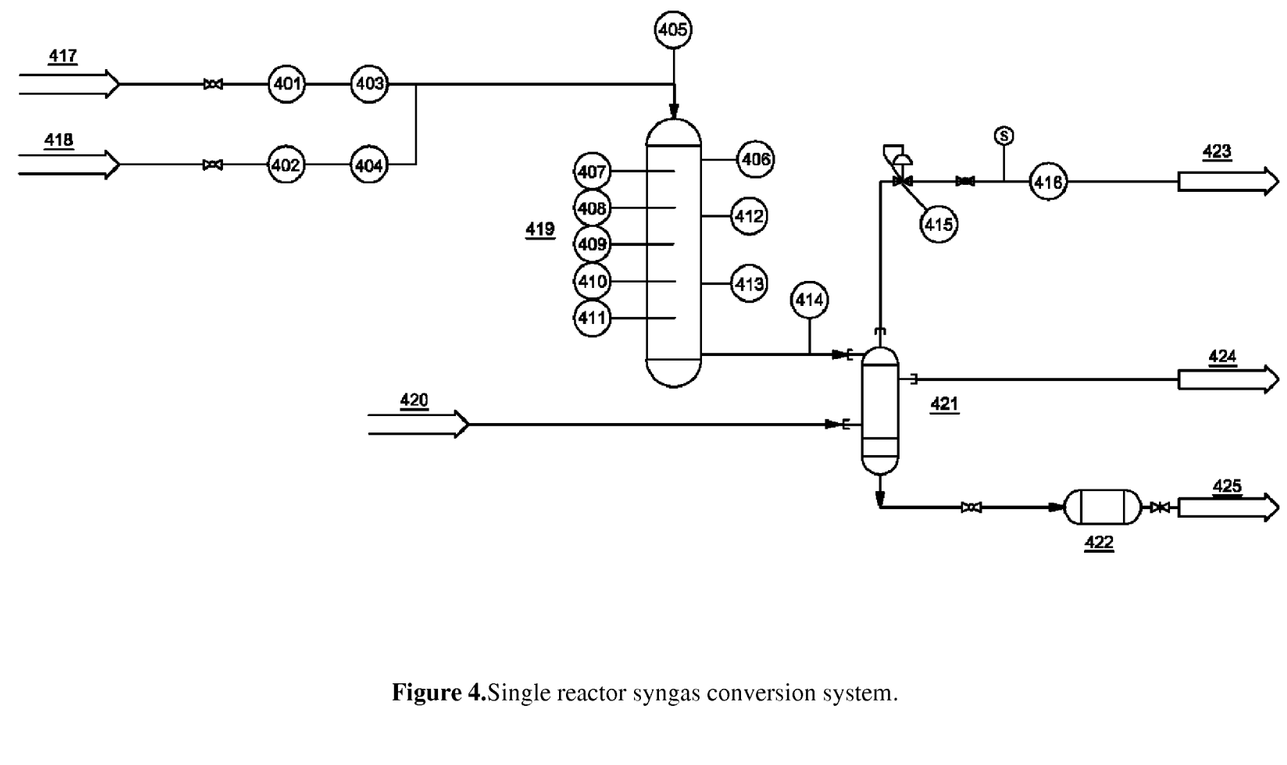
FIG. 4 describes the single reactor syngas conversion system.

FIG. 4 describes a single reactor syngas to dimethyl ether conversion system where carbon monoxide and hydrogen sources (417-418) are controlled by mass flow controllers (401-402) and measured by mass flow meters (403-404). The mixed syngas is converted in a single reactor (419) heated by heat tape and the product gasses pass through a condenser (421) chilled by a coolant loop (420, 424). Liquid products are collected in a sample cylinder (422) and removed for liquid analysis (425). Gas products pass through a back pressure regulator (415), are measured by a dry gas meter (416) and are vented for gas analysis (423). Pressure is monitored by a pressure transducer (406) and temperature is monitored by thermocouples (405, 407-414).

Figure 5:
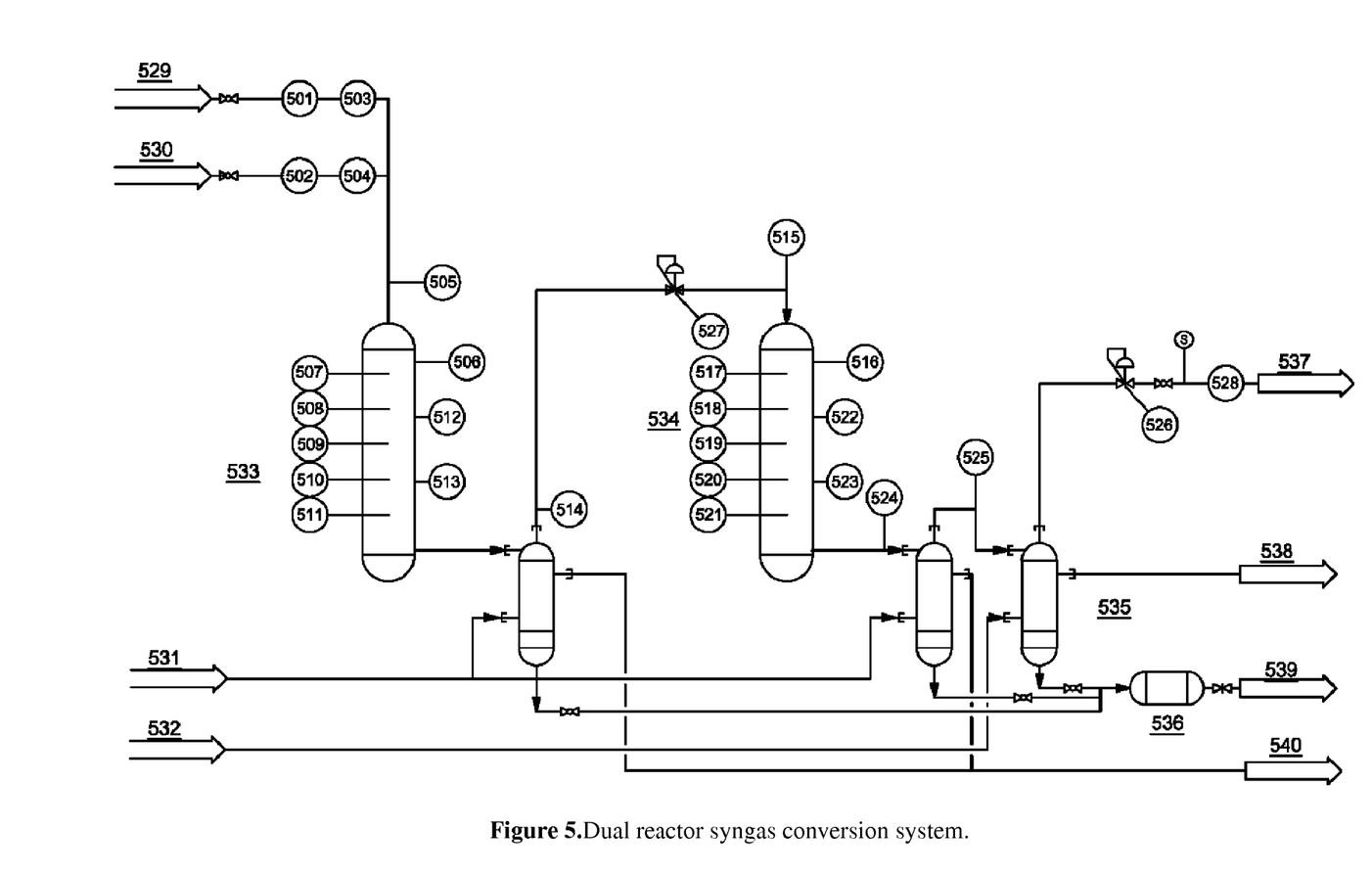
FIG. 5 describes the dual reactor syngas conversion system.

FIG. 5 describes a dual reactor syngas to gasoline conversion system where carbon monoxide and hydrogen sources (529-530) are controlled by mass flow controllers (501-502) and measured by mass flow meters (503-504). Mixed syngas is passes through the first reactor (533) and into a condenser cooled by cold house water (531, 540). Gas products pass a back pressure regulator (527) and are fed into a second reactor (534) and into the second cold house water condenser. Gas products from that condenser pass through a coolant loop (532, 538) chilled condenser (535) and any remaining gas passes through a back pressure regulator (526), is measured by a dry gas meter (528) and is vented from the system for gas analysis (537). Liquid from all condensers is collected in a sample cylinder (536) and removed from the system for liquid analysis (539). Pressure is monitored by pressure transducers (506, 517) and temperature is measured by thermocouples (505, 507-515, 517-525).

Figure 6:
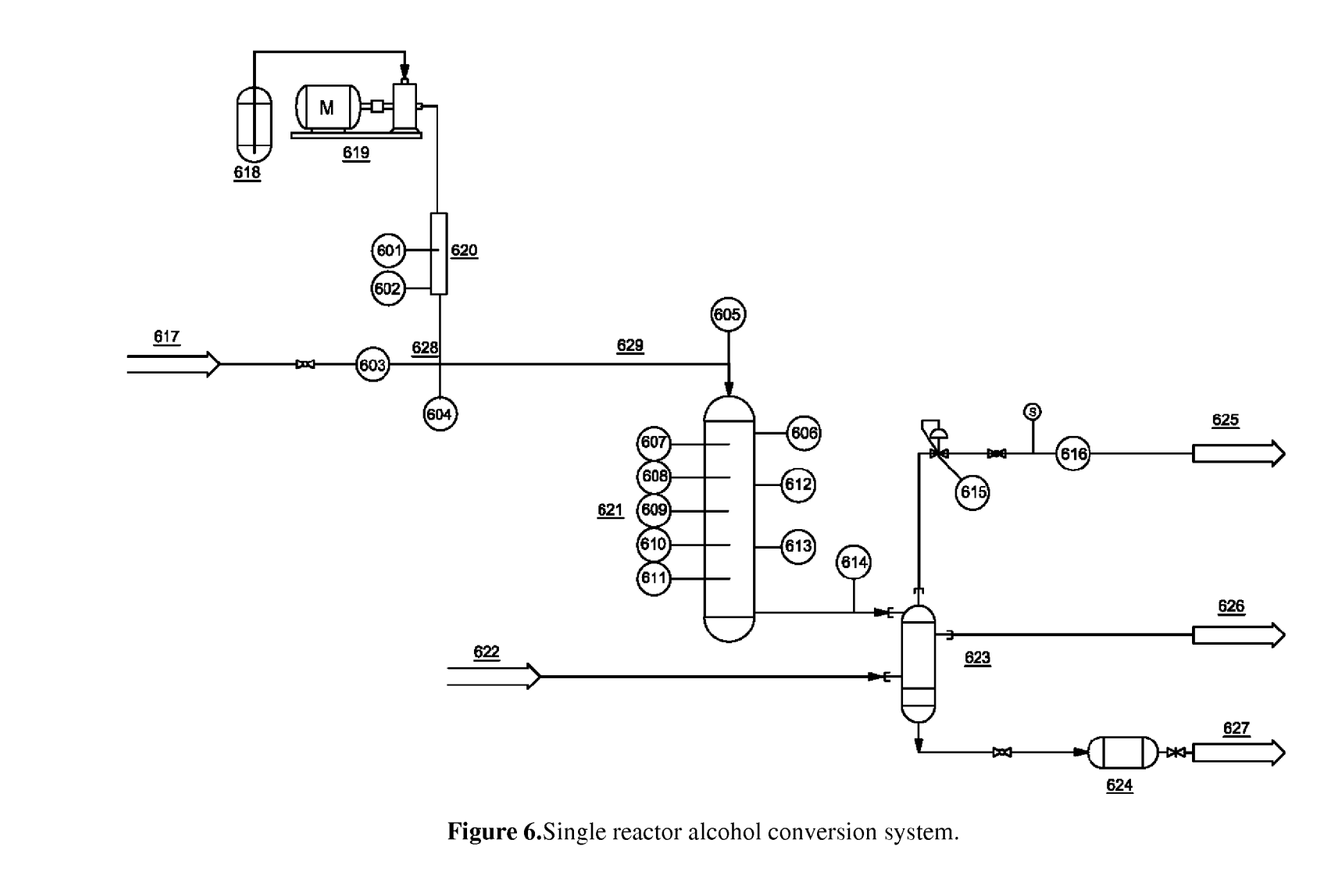
FIG. 6 describes the single reactor alcohol conversion system.

FIG. 6 describes a single reactor alcohol conversion system where a premixed feed of alcohols or alcohol and water is stored in a liquid reservoir (618). An HPLC pump (619) feeds the liquid into a vaporizer (620) heated with heat tape and can be mixed with an inert gas (617) controlled by a mass flow controller (603). Mixed gasses are heated by heat tape (628-629) and fed into the reactor (621) heated by heat tape. Products from the reactor pass into a condenser (623) chilled by a coolant loop (622, 626) and liquid products are collected in a sample cylinder (624) and removed for liquid analysis (627). Gas products pass through a back pressure regulator (615), are measured by a dry gas meter (616) and are vented from the system and analyzed (625). Pressure is monitored by a pressure transducer (606) and temperature monitored by thermocouples (601-602, 604-605, 607-614).

EXPERIMENTAL

Although the following experiments are described in detail, they are illustrative examples of the inventions described herein and not limitative of the remainder of the description.

Reagents and catalysts used were obtained from commercial sources such as Sigma Aldrich, Alfa Aesar, etc. or prepared through procedures well known to those with ordinary skill in the art.

Gas phase products were analyzed with a Varian MicroGC with four channels: a 20 m 5 A molecular sieve column with Ar carrier, a 20 m 5 A molecular sieve column with He carrier, a 10 m PPQ column with He carrier and an 8 m CBS column with He carrier. All channels used thermal conductivity detectors. Calibrations using external standards were performed for all identified compounds.

Liquid products were analyzed on an Agilent 6890 5973 GCMS system equipped with a JW1 DB624 column with dimensions of 30 m×250 μm×1.4 μm. The method ran at 1 ml/min flow, with oven temperature at 40° C. for the first two minutes followed by temperature ramp at 10° C./min to a temperature of 240° C. which was held for 10 minutes. The solvent delay was set at 5 minutes. Chemical identities of the obtained products were confirmed against a NIST 2011 library.

Experiment 1

The zeolite catalyst used in these examples was ZSM-5 in the acid form doped with 5 wt % Zn. Commercial HZSM-5 (provided by Tricat Inc., $SiO_2/Al_2O_3=23.5$) was doped with $Zn(NO_3)_2$ using the incipient wetness impregnation technique. The wetted catalyst was heated to 80° C. for 6 hours, dried at 120° C. for 6 hours and finally calcined at 600° C. for 6 hours. Gamma-alumina catalyst was obtained from a commercial source (Tricat Inc.) and used as received. The reactor system for this experiment, illustrated in FIG. 1, consisted of an ASA schedule 40 steel pipe reactor with a 10:1 form factor and 1.5 inch diameter, for an internal volume of approximately 0.5 L. Temperatures were measured by thermocouples running the length of the bed and measured from the center of the reactor. Pressure was monitored by a pressure transducer.

For this experiment the reactor was loaded with 25% (v/v) gamma-alumina and 75% Zn-ZSM-5. The catalysts were measured and homogenously mixed prior to loading the reactor. Total catalyst weight was approximately 300 g.

Methanol was introduced to the system via a HPLC pump and a vaporizer and then combined with a He carrier gas that was controlled by a mass flow controller. The methanol flow rates were varied from 0.5 to 5 mL/min and the He flow rates from 0.15 to 1 SLPM.

The pressure inside the reactor was kept at nominally atmospheric pressure. Temperatures inside the reactor were controlled so that the inlet temperature was 200° C. and the temperature increased approximately linearly to the outlet which was at 450° C.

After exiting the reactor the product stream passed through a condenser to separate out the liquid products, and then the remaining gas stream either left the system through a dry gas meter or was recycled through the reactor using a recirculation pump. Liquid samples were massed and the composition determined through GC-MS using the procedure described above. Gas samples were taken at regular intervals and the gas composition was determined with GC analysis as described above.

Selected samples that show the results of process variable changes are shown in Table 1A. The system efficiency is reported as the organic liquid yield, which is ratio of the total organic liquid product mass divided by the organic fraction of the input methanol.

$$\text{organic liquid yield efficiency} = \frac{mass_{org\,liq}}{mass_{MeOH} * 0.438} * 100\%$$

Typical gas and liquid product distributions for all experiments with a methanol feedstock are shown in Table 1B for reference.

TABLE 1A

| | Sample # | | | | |
|---|---|---|---|---|---|
| | 1 | 2 | 3 | 4 | 5 |
| Methanol GHSV ($h^{-1}$) | 33 | 67 | 134 | 67 | 67 |
| He GHSV ($h^{-1}$) | 120 | 18 | 18 | 18 | 18 |
| Total Input GHSV ($h^{-1}$) | 153 | 85 | 152 | 85 | 85 |
| Approximate Recirculation Ratio | 0 | 0 | 0 | 0.75 | 1.5 |
| Organic Liquid Yield Efficiency (%) | 60.4 | 57.8 | 57.6 | 59.6 | 57.8 |

TABLE 1B

| Component | Wt % |
|---|---|
| Water | 55.7 |
| $H_2$ | 0.5 |
| CO | 0.1 |
| $CO_2$ | 0.2 |
| Methane | 0.6 |
| Ethylene | 0.3 |
| Ethane | 0.3 |
| Propane | 0.4 |
| Dimethyl Ether | 4.6 |
| i-Butane | 2.9 |
| n-Butane | 0.7 |
| Pentane | 0.6 |
| Benzene | 0.3 |
| Toluene | 4.3 |
| C8 aromatics | 11.9 |
| C9 aromatics | 9.4 |
| C10 aromatics | 5.6 |
| C11 aromatics | 0.9 |
| C12 aromatics | 0.6 |

Experiment 2

The same reactor system from EXPERIMENT 1 was used except a gradient composition mixed bed catalyst was used. The first third of the reactor was packed with homogenously mixed 75% gamma-alumina and 25% Zn-ZSM-5 (v/v) while the rest of the reactor was packed with 25% gamma-alumina and 75% Zn-ZSM-5. The temperature varied linearly from 200° C. at the inlet to 450° C. at the outlet, and the pressure was maintained at nominally atmospheric pressure. No inert diluent gas was used in these tests. The effects of other process variables are detailed in Table 2.

TABLE 2

| | Sample # | | | | | | | |
|---|---|---|---|---|---|---|---|---|
| | 6 | 7 | 8 | 9 | 10 | 11 | 12 | 13 |
| Methanol GHSV ($h^{-1}$) | 67 | 67 | 67 | 67 | 134 | 200 | 267 | 334 |
| Approximate Recirculation Ratio | 0 | 1 | 2 | 4 | 0.9 | 0.6 | 0.5 | 0.4 |
| Organic Liquid Yield (%) | 66.6 | 72.4 | 68.1 | 67.5 | 59.8 | 53.0 | 55.5 | 44.9 |

Experiment 3

This experiment used the two reactor system as described in FIG. 2. Reactor 1 was a mixed-bed, gradient reactor with the first third consisting of 75% gamma-alumina and 25% Zn-ZSM-5 (v/v) while the rest of the reactor was packed with 25% gamma-alumina and 75% Zn-ZSM-5. Temperatures in the first reactor varied linearly from 200° C. at the inlet to 400° C. at the outlet. Reactor 2 was packed with Zn-ZSM-5 only and was held at nominally atmospheric pressure and 400° C. The pressure of the first reactor was varied as shown in Table 3. A hydrogen separation membrane was also included in between the reactors for some tests. Sample 17 included a recirculation loop that fed the product gas into the system immediately before the separation membrane.

TABLE 3

| | Sample # | | | |
|---|---|---|---|---|
| | 14 | 15 | 16 | 17 |
| Methanol GHSV ($h^{-1}$) | 267 | 267 | 281 | 267 |
| Membrane Used | no | yes | yes | yes |
| Reactor Pressure (psig) | 0 | 30 | 80 | 35 |
| Recirculation Rate | 0 | 0 | 0 | 4.5 |
| Organic Liquid Yield (%) | 73.8 | 72.9 | 64.4 | 71.7 |
| Total Product Distribution (wt %) | | | | |
| Water | 47.7 | 50.3 | 49.1 | 56.2 |
| $H_2$ | 1.6 | 1.3 | 1.1 | 0.4 |
| CO | 2.7 | 1.6 | 2.7 | 1.3 |
| $CO_2$ | 4.0 | 4.9 | 2.5 | 0.4 |
| Hydrocarbons | 43.9 | 41.9 | 44.5 | 41.7 |
| Hydrocarbon Composition (wt %) | | | | |
| Methane | 4.4 | 4.3 | 6.8 | 4.0 |
| Ethylene | 0.3 | 0.6 | 0.3 | 0.1 |
| Ethane | 1.9 | 0.4 | 1.7 | 1.6 |
| Propane | 0.3 | 0.4 | 0.3 | 0.0 |
| Dimethyl Ether | 13.4 | 5.8 | 7.2 | 6.8 |
| i-Butane | 7.5 | 5.1 | 3.8 | 2.1 |
| n-Butane | 2.9 | 1.4 | 1.3 | 1.1 |
| Pentane | 0.0 | 1.7 | 1.1 | 0.0 |
| Benzene | 0.5 | 0.5 | 0.5 | 0.2 |
| Toluene | 6.0 | 5.4 | 5.4 | 4.4 |
| C8 Aromatics | 22.6 | 22.7 | 21.5 | 26.6 |
| C9 Aromatics | 23.1 | 26.3 | 24.5 | 30.9 |
| C10 Aromatics | 12.9 | 20.3 | 20.4 | 18.7 |
| C11 Aromatics | 1.7 | 2.8 | 2.5 | 1.9 |
| C12+ Aromatics | 2.5 | 2.4 | 2.6 | 1.5 |

Experiment 4

The reactor system for this experiment is illustrated in FIG. 1. For this experiment the reactor was loaded with 50% (v/v) gamma-alumina and 50% Zn-ZSM-5. The catalysts were measured and homogenously mixed prior to loading the reactor. Total catalyst weight was approximately 300 g.

Ethanol was introduced to the system via a HPLC pump and a vaporizer. The ethanol flow rate was 1 mL/min which translates to a GHSV of 46 $h^{-1}$.

Temperatures inside the reactor were controlled so that the inlet temperature was 200° C. and the temperature increased approximately linearly to the outlet which was at 400° C. After exiting the reactor the product stream passed through a condenser to separate out the liquid products, and then the remaining gas stream left the system through a dry gas meter. Liquid samples were massed and the composition determined through GC-MS using the procedure described above. Gas samples were taken at regular intervals and the gas composition was determined with GC analysis as described above.

Selected samples that show typical results and the influence of pressure changes are shown in Table 4. The system efficiency is reported as the organic liquid yield, which is ratio of the total organic liquid product mass divided by the organic fraction of the input ethanol.

$$\text{organic liquid yield efficiency} = \frac{mass_{org\,liq}}{mass_{EtOH} * 0.609} * 100\%$$

TABLE 4

| | Sample # | |
|---|---|---|
| | 18 | 19 |
| Reactor Pressure (psi) | 5 | 100 |
| Organic Liquid Yield Efficiency (%) | 60.4 | 57.4 |
| Total Product Distribution (wt %) | | |
| Water | 37.0 | 39.0 |
| $H_2$ | 1.2 | 1.0 |
| CO | 0.1 | 0.3 |
| $CO_2$ | 0.2 | 0.8 |
| Hydrocarbons | 61.5 | 59.0 |
| Hydrocarbon Composition (wt %) | | |
| Methane | 0.7 | 1.0 |
| Ethylene | 1.0 | 0.6 |
| Ethane | 1.6 | 3.3 |
| Propane | 17.2 | 20.2 |
| i-Butane | 13.7 | 6.5 |
| n-Butane | 4.3 | 2.4 |
| Pentane | 0.0 | 2.8 |
| Benzene | 1.8 | 1.8 |
| Toluene | 15.0 | 12.0 |
| C8 Aromatics | 24.8 | 21.3 |
| C9 Aromatics | 12.6 | 13.2 |
| C10 Aromatics | 4.0 | 7.0 |
| C11 Aromatics | 0.9 | 3.0 |
| C12+ Aromatics | 2.4 | 4.9 |

Experiment 5

The same reactor system from EXPERIMENT 4 was used except the feedstock was mixed methanol and ethanol. The alcohols were mixed in a common reservoir and pumped as a single feed. The temperature varied linearly from 225° C. at the inlet to 400° C. at the outlet, and the pressure was maintained at nominally atmospheric pressure. Efficiency was calculated similarly to the equation in EXPERIMENT 4 but accounting for the mixed nature of the feed. The typical results of the feedstock variations are shown in Table 5.

TABLE 5

| | Sample # | |
|---|---|---|
| | 20 | 21 |
| Methanol:Ethanol Ratio of Feed | 1:1 | 3:1 |
| Organic Fraction of Feed (%) | 53.8 | 49.4 |
| Organic Liquid Yield (%) | 64.4 | 67.9 |
| Total Product Distribution (wt %) | | |
| Water | 51.4 | 49.1 |
| $H_2$ | 0.6 | 1.0 |
| CO | 0.1 | 0.2 |
| $CO_2$ | 0.2 | 0.3 |
| Hydrocarbons | 47.7 | 49.4 |
| Hydrocarbon Composition (wt %) | | |
| Methane | 0.6 | 1.1 |
| Ethylene | 1.0 | 1.5 |
| Ethane | 0.9 | 1.1 |
| Propane | 1.1 | 1.7 |
| Dimethyl Ether | 10.7 | 14.5 |
| i-Butane | 9.2 | 11.9 |
| n-Butane | 2.9 | 3.0 |
| Pentane | 1.0 | 2.1 |

TABLE 5-continued

| | Sample # | |
|---|---|---|
| | 20 | 21 |
| Benzene | 1.3 | 1.0 |
| Toluene | 14.0 | 11.5 |
| C8 Aromatics | 28.2 | 24.0 |
| C9 Aromatics | 17.7 | 16.3 |
| C10 Aromatics | 8.6 | 8.9 |
| C11 Aromatics | 1.1 | 0.5 |
| C12+ Aromatics | 1.8 | 0.9 |

Experiment 6

For this experiment the same reactor setup was used as in the previous two experiments. The feedstock was a mixture of ethanol and water which were mixed in a single reservoir and pumped together. The flow rates were adjusted so that the ethanol GHSV was approximately 46 h$^{-1}$ for all tests. The reactor temperature varied linearly from 250° C. at the inlet to 400° C. at the outlet, and the system was maintained at atmospheric pressure. Results of the variations of the feed ethanol/water ratio are shown in Table 6. The organic liquid yield is calculated as in EXPERIMENT 4 and only considers the ethanol content of the feed.

TABLE 6

| | Sample # | |
|---|---|---|
| | 22 | 23 |
| Ethanol:Water Ratio of Feed | 9:1 | 1:1 |
| Organic Liquid Yield (%) | 65.3 | 60.4 |
| Total Product Distribution (wt %) | | |
| Water | 47.3 | 73.3 |
| $H_2$ | 1.0 | 0.7 |
| CO | 0.1 | 0.2 |
| $CO_2$ | 0.2 | 0.8 |
| Hydrocarbons | 51.5 | 25.1 |
| Hydrocarbon Composition (wt %) | | |
| Methane | 0.6 | 1.1 |
| Ethylene | 1.0 | 2.7 |
| Ethane | 1.4 | 1.3 |
| Propane | 10.4 | 13.0 |
| i-Butane | 8.5 | 14.6 |
| n-Butane | 2.3 | 4.6 |
| Pentane | 2.0 | 3.5 |
| Benzene | 1.7 | 1.0 |
| Toluene | 16.2 | 11.2 |
| C8 Aromatics | 29.0 | 21.8 |
| C9 Aromatics | 17.6 | 18.7 |
| C10 Aromatics | 6.1 | 4.7 |
| C11 Aromatics | 1.4 | 0.7 |
| C12+ Aromatics | 2.0 | 1.1 |

Experiment 7

The conversion of a $H_2$/CO mixture utilized the reactor system shown in FIG. 4, with the same sized reactor and components as in the previous experiments. Catalyst composition varied between tests but always including the same gamma-alumina and Zn-ZSM-5 used previously, and additionally the CO reduction catalyst Cu—ZnO (Unicat). Sample 24 used a reactor containing equal volume portions of gamma-alumina, Zn-ZSM-5 and Cu—ZnO mixed homogenously. Sample 25 consisted of equal volumes of gamma-alumina and Cu—ZnO for the first half of the reactor, then only Zn-ZSM-5 in the second half. In all cases the catalyst was reduced for 16 hours at 180° C. with a 5% $H_2$ gas stream (balance $N_2$) flowing at 0.5 SLPM, then for 1 hour at the same temperature with 100% $H_2$. The reactor was always kept in a reducing environment or this procedure was repeated before testing.

The reactor temperatures were controlled with an approximately linear gradient with the inlet cooler than the outlet. The effect of the temperature gradient size is shown in Table 7.

TABLE 7

|  | Sample # | |
| --- | --- | --- |
|  | 24 | 25 |
| $H_2$/CO Feed Ratio | 2/1 | 2/1 |
| Total GHSV ($h^{-1}$) | 200 | 174 |
| Reactor Pressure (psig) | 300 | 285 |
| Reactor Temperature (° C.) | 225-300 | 200-420 |
| CO conversion (%) | 86.5 | 67.0 |
| Total Product Distribution (wt %) | | |
| Hydrocarbon | 19.5 | 15.1 |
| $H_2$ | 7.2 | 9.2 |
| CO | 13.1 | 29.9 |
| $CO_2$ | 55.6 | 40.0 |
| $H_2O$ | 4.5 | 5.7 |
| Hydrocarbon Composition (wt %) | | |
| Methane | 4.3 | 12.9 |
| Ethane | 17.0 | 21.5 |
| Ethylene | 0.0 | 0.0 |
| Propane | 27.7 | 37.7 |
| i-butane | 29.4 | 25.2 |
| n-butane | 8.0 | 0.0 |
| C6+ aliphatic | 1.8 | 0.0 |
| Benzene | 0.0 | 0.0 |
| Toluene | 0.4 | 0.0 |
| C8 aromatic | 0.4 | 0.0 |
| C9 aromatic | 0.8 | 0.4 |
| C10 aromatic | 4.1 | 1.6 |
| C11+ aromatic | 2.9 | 0.7 |

Experiment 8

This experiment utilized a two reactor syngas conversion system as shown in FIG. 5. The first reactor employed a mixed catalyst for syngas conversion to dimethyl ether which was then converted to larger hydrocarbons in a second reactor. The catalyst in Reactor 1 was homogenously mixed Cu—ZnO and gamma-alumina, each one half by volume. The catalyst in the second reactor was all Zn-ZSM-5. Pressures around 300 psi in the first reactor encouraged syngas conversion while ambient pressure in the second reactor favored aromatic hydrocarbon production. The feed $H_2$/CO ratio was varied from 1 to 2. Typical results of changing the process variables are shown in Table 8.

TABLE 8

|  | Sample # | |
| --- | --- | --- |
|  | 26 | 27 |
| $H_2$/CO Feed Ratio | 2/1 | 1/1 |
| Total GHSV ($h^{-1}$) | 174 | 230 |
| Reactor 1 Temperature (° C.) | 250 | 175-275 |
| Reactor 2 Temperature (° C.) | 400 | 450 |
| CO Conversion (%) | 60.9 | 64.9 |
| Total Product Distribution (wt %) | | |

TABLE 8-continued

|  | Sample # | |
| --- | --- | --- |
|  | 26 | 27 |
| Hydrocarbon | 17.5 | 16.0 |
| $H_2$ | 8.8 | 2.7 |
| CO | 30.4 | 29.5 |
| $CO_2$ | 34.2 | 44.1 |
| $H_2O$ | 9.2 | 7.7 |
| Hydrocarbon Composition (wt %) | | |
| Methane | 7.5 | 6.2 |
| Ethane | 4.6 | 4.3 |
| Ethylene | 0.1 | 1.7 |
| Propane | 22.7 | 18.3 |
| i-butane | 26.5 | 10.4 |
| n-butane | 0.0 | 0.0 |
| Benzene | 0.1 | 1.2 |
| Toluene | 4.1 | 11.0 |
| C8 aromatic | 13.1 | 23.8 |
| C9 aromatic | 11.2 | 15.0 |
| C10 aromatic | 7.4 | 6.4 |
| C11+ aromatic | 2.6 | 1.7 |

Experiment 9

The type of system described in EXPERIMENT 8 can also be used to produce dimethyl ether as an end product. A single reactor was loaded with the top ¾ homogenously mixed Cu—ZnO and gamma-alumina, each one half by volume, and the bottom ¼ was pure gamma-alumina. The $H_2$/CO ratio of the feed was kept between 1 and 1.3 to promote the consumption of water via the water gas shift reaction to drive the thermodynamics forward. Pressures around 300 psi encouraged syngas production and facilitated condensation of the dimethyl ether and some $CO_2$ in a condenser held between −30 and −40° C.

TABLE 9

|  | Sample # 28 |
| --- | --- |
| $H_2$/$CO_2$ Feed Ratio | 1.3 |
| Reactor Temperature (° C.) | 250-275 |
| Total Product Distribution (wt %) | |
| $H_2$ | 4.0 |
| CO | 40.3 |
| $CO_2$ | 31.7 |
| Methane | 0.1 |
| Dimethyl Ether | 23.1 |
| Dimethyl Ether Production Yield (%) | 54 |
| Dimethyl Ether Captured (%) | 89 |
| DME/$CO_2$ Capture Ratio | 2.05 |

Experiment 10

The type of system tested in EXPERIMENT 9 could also be used with a syngas feed that contained a contaminate from the syngas production such as carbon dioxide or nitrogen. The same reactor as in EXPERIMENT 9 was used for tests with carbon dioxide. A reactor loaded with the top ⅞ as CuO—ZnO and gamma-alumina each one half by volume and the bottom ⅛ was pure gamma-alumina. In all cases the internal reactor volume was 0.5 L. Additional process variables and results are detailed in Table 10.

TABLE 10

| | Sample # | | |
|---|---|---|---|
| | 29 | 30 | 31 |
| Feed Rate (SLPM) | | | |
| $H_2$ | 1.8 | 1.6 | 1.3 |
| CO | 0.3 | 0.5 | 0.7 |
| $CO_2$ | 0.6 | 0 | 0 |
| $N_2$ | 0 | 1.8 | 1.8 |
| Reactor Pressure (psig) | 284 | 286 | 393 |
| Reactor Temperature (° C.) | 230-260 | 160-260 | 140-270 |
| Total Product Distribution (wt %) | | | |
| $H_2$ | 64.7 | 36.9 | 28.2 |
| CO | 8.7 | 7.1 | 9.9 |
| $CO_2$ | 24.6 | 2.5 | 3.8 |
| $N_2$ | 0 | 54.9 | 54.2 |
| Dimethyl Ether | 2.0 | 2.1 | 3.0 |
| CO Conversion (%) | 54 | 54 | 58 |
| Dimethyl Ether Selectivity (%) | 89 | 62 | 61 |

Experiment 11

To test the feasibility of dimethyl ether conversion to larger hydrocarbons pure dimethyl ether was fed into a reactor containing only Zn-ZSM-5. The reactor was kept at atmospheric pressure and the dimethyl ether gas was fed at a GHSV of 50 $h^{-1}$. The results of temperature variations are shown in Table 11.

TABLE 11

| | Sample # | | | |
|---|---|---|---|---|
| | 32 | 33 | 34 | 35 |
| Temperature (° C.) | 350 | 400 | 450 | 500 |
| Organic Liquid Yield Efficiency (%) | 52.1 | 51.9 | 62.4 | 60.6 |
| Total Product Distribution (wt %) | | | | |
| Water | 39.7 | 36.7 | 27.2 | 23.8 |
| $H_2$ | 0.9 | 1.7 | 2.7 | 3.4 |
| CO | 0.2 | 0.5 | 0.8 | 2.2 |
| $CO_2$ | 0.4 | 1.7 | 4.7 | 13.5 |
| Hydrocarbons | 49.2 | 48.3 | 54.2 | 52.2 |
| Unreacted Dimethyl Ether | 9.54 | 11.18 | 10.34 | 5.0 |
| Hydrocarbon Composition (wt %) | | | | |
| Methane | 1.4 | 3.1 | 5.6 | 9.5 |
| Ethylene | 0.2 | 0.4 | 0.5 | 0.5 |
| Ethane | 0.9 | 1.6 | 2.7 | 4.2 |
| Propane | 0.1 | 0.3 | 0.0 | 0.0 |
| i-Butane | 7.9 | 15.2 | 4.2 | 2.6 |
| n-Butane | 1.8 | 5.0 | 2.2 | 2.2 |
| Pentane | 0.0 | 1.8 | 3.4 | 3.6 |
| Benzene | 1.1 | 1.6 | 3.0 | 4.0 |
| Toluene | 9.8 | 12.6 | 15.5 | 14.5 |
| C8 Aromatics | 27.1 | 26.9 | 28.6 | 24.2 |
| C9 Aromatics | 23.8 | 17.7 | 18.7 | 17.3 |
| C10 Aromatics | 18.2 | 10.5 | 11.0 | 10.9 |
| C11 Aromatics | 2.8 | 1.1 | 1.8 | 2.3 |
| C12+ Aromatics | 4.8 | 2.3 | 3.0 | 4.2 |

Experiment 12

To test the feasibility of producing aromatic hydrocarbons from ethylene, propylene, and their mixtures, a gas containing one or both components was fed into a reactor containing only Zn-ZSM-5. The reactor had a volume of 0.5 L, was kept at atmospheric pressure, and the olefin feed was fed at a GHSV of 90-120 $h^{-1}$. The results of feed composition and temperature variations are shown in Table 12.

TABLE 12

| | Sample # | | | |
|---|---|---|---|---|
| | 36 | 37 | 38 | 39 |
| Ethylene Flow Rate (SLPM) | 1.0 | 0.5 | 0.5 | 0.25 |
| Propylene Flow Rate (SLPM) | 0.0 | 0.5 | 0.25 | 0.5 |
| Temperature (° C.) | 450 | 450 | 350 | 350 |
| Organic Liquid Yield Efficiency (%) | 39.2 | 36.8 | 32.9 | 31.7 |
| Product Composition (wt %) | | | | |
| Hydrogen | 2.1 | 2.1 | 1.2 | 0.9 |
| Methane | 8.3 | 7.6 | 2.7 | 2.0 |
| Ethylene | 0.0 | 0.0 | 0.4 | 0.2 |
| Ethane | 22.4 | 14.7 | 4.5 | 2.7 |
| Propylene | 13.2 | 17.8 | 20.5 | 21.3 |
| Propane | 0.0 | 0.0 | 0.0 | 0.0 |
| i-Butane | 1.7 | 2.6 | 11.6 | 12.9 |
| n-Butane | 1.4 | 2.3 | 5.0 | 5.8 |
| Pentane | 0.0 | 0.6 | 3.1 | 4.1 |
| Benzene | 1.7 | 4.7 | 1.9 | 1.7 |
| Toluene | 3.7 | 8.0 | 4.2 | 5.3 |
| C8 Aromatics | 8.2 | 13.6 | 9.8 | 12.2 |
| C9 Aromatics | 7.9 | 6.8 | 9.4 | 10.3 |
| C10 Aromatics | 7.5 | 3.9 | 9.9 | 8.5 |
| C11 Aromatics | 6.3 | 4.8 | 8.2 | 7.3 |
| C12+ Aromatics | 11.9 | 10.4 | 7.7 | 4.8 |

Experiment 13

Catalysts containing $CeO_2$ and $MnO_2$ deposited on alumina are prepared by impregnation supports with aqueous solutions of precursors using the incipient wetness technique. The impregnated samples are then dried at 121° C. for 12 h and then calcined at 450° C. for 3 h in a stream of air. The ketonization is performed in a typical fixed bed tubular quartz reactor with 1 g of catalyst and the reactants are delivered to the reactor using a pump with liquid hourly space velocity (LHSV): 0.25 cc/g catalyst/h. The ketonization process is performed at a temperature range of 250-450° C. Quantitative conversion of the acid was noted at 350° C. in the presence of the following catalysts: 10 and 20 wt. percent $MnO_2/Al_2O_3$, 20 wt. percent $MnO_2/TiO_2$, 20 wt. percent $CeO_2Al_2O_3$ and 20 wt.-% $CeO_2/TiO_2$. The highest activity is exhibited by alumina supported catalysts. At 325° C. and 350° C., 96% yield of acetone was obtained from 20% $MnO_2$ on alumina.

Experiment 14

In a cylindrical reactor about 5.5 L in volume, 3765 gm of 3.2×3.2 mm tablets of CuO—ZnO catalyst is added and the reactor purged with nitrogen. Isopropanol containing 2% water is pumped over the catalyst bed at 10 L/hr along with hydrogen gas at 2000 SLPH (Standard L/hr) as the pressure is around 435 psig. The catalyst bed is heated to 100° C. and catalyst reduced for 3 hours. After reduction of the catalyst, isopropanol flow is raised to 25 L/hr and hydrogen flow rate to about 550 SLPH with the reactor pressure at about 290 psig. The reactor temperature is raised to 140° C. and acetone with 2% water is passed through the reactor at 1.64 SLPH. The temperature of the lower part of the reactor rose to 160° C. due to exotherm. The reaction is continued with the reactor top at 140° C. and pressure at 290 psig as product is collected. GC analysis indicates 98.5% acetone conversion with 98.6 selectivity for isopropanol. Morizane et al U.S. Pat. No. 8,283,504 B2
Energy Analysis calorimetry was performed on representative samples of the liquid products in order to measure the energy content of the fuel. For reference, methanol and ethanol have energy densities of 22.6 kJ/g and 29.7 kJ/g, respectively. The energy density of gasoline is about 45 kJ/g. Results of the analysis are reported in Table 13 and show that the fuels produced in this system are comparable to modern petroleum derived fuels.

TABLE 13

| Experiment # | Sample # | Feedstock | Reactor System | Energy Density (kJ/g) |
|---|---|---|---|---|
| 1 | 3 | methanol | single reactor homogenous catalyst | 43.0 |
| 2 | 10 | methanol | single reactor gradient catalyst | 43.1 |
| 2 | 11 | methanol | single reactor gradient catalyst | 43.0 |
| 2 | 12 | methanol | single reactor gradient catalyst | 43.1 |
| 2 | 13 | methanol | single reactor gradient catalyst | 42.8 |
| 3 | 14 | methanol | two reactor gradient catalyst | 42.6 |
| 3 | 15 | methanol | two reactor gradient catalyst | 42.7 |
| 3 | 16 | methanol | two reactor gradient catalyst | 42.6 |
| 3 | 17 | methanol | two reactor gradient catalyst | 42.4 |
| 7 | 24 | syngas | single reactor homogenous catalyst | 44.7 |
| 8 | 27 | syngas | two reactor homogenous catalyst | 42.3 |

What is claimed is:

1. A method to synthesize aromatic hydrocarbons in the gasoline boiling range, comprising:
    reacting a feedstock selected from the group consisting of methanol and ethanol, in a single reactor over a mixed catalyst bed charged with a dehydration catalyst and a zeolite catalyst,
    wherein a gradient composition mixed catalyst bed is used wherein the first third of the reactor is packed with a homogenously mixed 75% dehydration catalyst and 25% zeolite catalyst v/v while the rest of the reactor is packed with 25% dehydration catalyst and 75% zeolite catalyst,
    wherein a temperature inside the reactor is varied linearly from 200° C. at the inlet to 450° C. at the reactor outlet, wherein gas hourly space velocity, GHSV, is between 67 and 334 $h^{-1}$, and wherein the dehydration catalyst is gamma alumina and the zeolite catalyst is ZSM-5.

2. The method of claim 1, where the gamma alumina has a silica/alumina ratio of around 23.

3. The method of claim 1, wherein the zeolite catalyst is doped with a transition metal element in the range of 1-10 wt. %.

4. The method of claim 3, wherein said transition metal is zinc.

5. The method of claim 1, wherein the feedstock is methanol.

6. The method of claim 1, wherein the feedstock is ethanol.

7. The method of claim 6, wherein the ethanol contains water not removed by distillation or other processes.

8. The method of claim 7, where the ethanol contains water at concentrations between 1 percent and 99 percent.

9. The method of claim 1, wherein the feedstock is a mixture of methanol and ethanol.

10. The method of claim 1, wherein the single reactor is configured as a portable system for transport and deployment to locations where sources are available for feedstock synthesis.

11. The method of claim 1, wherein the single reactor is configured as a portable system for transport and deployment to locations where ethanol is available.

12. The method of claim 1, wherein a second reactor, filled with the zeolite catalyst, is added after the first reactor to further convert lower molecular weight product molecules from the first reactor.

13. The method of claim 12, wherein a hydrogen separator is utilized in between the first reactor and the second reactor to remove hydrogen produced in the first reactor.

14. The method of claim 13, wherein product gases from the second reactor are recycled into an inlet of the hydrogen separator after removal of condensable products.

15. The method of claim 1, wherein the temperature inside the single reactor varies along its length.

16. The method of claim 1 where the ratio of dehydration catalyst to zeolite catalyst is varied along the length of the reactor.

* * * * *